(12) United States Patent
Bouchard et al.

(10) Patent No.: US 9,107,871 B2
(45) Date of Patent: Aug. 18, 2015

(54) LHRH—ANTAGONISTS IN THE TREATMENT OF FERTILITY DISORDERS

(75) Inventors: Philippe Bouchard, Paris (FR); Rene Frydman, Paris (FR); Paul Devroey, Aalst (BE); Klaus Diedrich, Grostrasse-Sarau (DE); Jurgen Engel, Alzenau (DE)

(73) Assignee: ZENTARIS IVP GMBH, Frankfurt am Main (DE)

( * ) Notice: Subject to any disclaimer, the term of this patent is extended or adjusted under 35 U.S.C. 154(b) by 1264 days.

(21) Appl. No.: 12/941,629

(22) Filed: Nov. 8, 2010

(65) Prior Publication Data

US 2011/0306547 A1 Dec. 15, 2011

Related U.S. Application Data

(63) Continuation of application No. 08/786,937, filed on Jan. 22, 1997, now abandoned.

(60) Provisional application No. 60/011,272, filed on Feb. 7, 1996.

(51) Int. Cl.
*A61K 38/09* (2006.01)
*C12M 3/00* (2006.01)

(52) U.S. Cl.
CPC ............... *A61K 38/09* (2013.01); *C12M 21/06* (2013.01)

(58) Field of Classification Search
None
See application file for complete search history.

(56) References Cited

U.S. PATENT DOCUMENTS

| | | | |
|---|---|---|---|
| 5,663,145 | A | 9/1997 | Engel |
| 6,022,860 | A | 2/2000 | Engel |
| 6,077,523 | A | 6/2000 | Deghenghi |
| 6,319,192 | B1 | 11/2001 | Engel |

FOREIGN PATENT DOCUMENTS

| | | |
|---|---|---|
| EP | 0788799 | 10/1998 |
| WO | 99/55357 | 11/1999 |
| WO | 00/59542 | 10/2000 |

OTHER PUBLICATIONS

Kelch et al., The Journal of Clinical Investigation, 1973 52: 1122-1128.*
Foulot et al., Fertil. Steril. 1989; 52: 617-621.*
Frydman et al., Fertil Steril. 1991; 56: 923-927.*
Frydman et al., Contraception-Fertilite-Sexualite, 1990; 18: 605-606—English translation attached: 8 pages total.*
Paulson et al., Journal of Assisted Reproduction and Genetics, 1994; 11: 28-32.*
Balmaceda et al., Contraception, 1981; 24: 275-281.*
Albano et al., "Hormonal Profile During the Follicular Phase in Cycles Stimulated with a Combination of Human Menopausal Gonadotrophin and Gonadotrophin-Releasing Hormone Antagonist (Cetrorelix)," Human Reproduction, vol. 11, No. 10, pp. 2114-2118, (1996).
Albano et al., "Comparison of different doses of gonadotropin-releasing hormone antagonist Cetrorelix during controlled ovarian hyperstimulation," Fertil. Steril., (Abstract), vol. 67, No. 5, p. 917-22, (May 1997).
Awonuga et al., "In Vitro Fertilization with Low-Dose Clomiphene Citrate Stimulation in Women Who Respond Poorly to Superovulation," Journal of Assist Reprod. Genetics, vol. 14, No. 9, pp. 503-507; (Oct. 1997).
Baril et al., "A new method for controlling the precise time of occurrence of the preovulatory gonadotropin surge in superovulated goats," Theriogenology, vol. 45, No. 3, p. 697-706, (Feb. 1996).
Deghenghi et al., "Antarelix (EP 24332) a novel water soluble LHRH antagonist," Biomed. Pharmacother., Europeptides (Argenteuil, France), vol. 47 ( No. 2-3), p. 107110, (1993).
Diedrich et al., "Suppression of the Endogenous Luteinizing Hormone Surge by the Gonadotrophin-Releasing Hormone Antagonist Cetrorelix During Ovarian Stimulation," Human Reproduction, vol. 9, No. 5, pp. 788-791, (May 1994).
Diedrich et al., "Suppression of the Endogenous Luteinizing Hormone Surge by the Gonadotrophin-Releasing Hormone Antagonist Cetrorelix During Ovarian Stimulation," Human Reproduction, vol. 9, No. 5, pp. 788-791, (May 1995).
Duijkers et al., "Single and multiple dose pharmacokinetics and pharmacodynamics of the gonadotrophin-releasing hormone antagonist Cetrorelix in healthy female volunteers," Human Reproduction, European Society for Human Reproduction and Embryology, vol. 13, No. 9, pp. 2392-2398, (1998).
Felberbaum et al., "Hormone Profiles and Pituitary Response Under Ovarian Stimulation With HMG and GnRH Antagonists (Cetrorelix)," Human Reproduction, vol. 9, No. 4, p. 13, (1994).
Felberbaum et al., Eur. J. Obstet. Gynecol. Reprod. Biol., vol. 61, No. 2, pp. 151-515, (1995).
Felberbaum et al., Huam Repord. vol. 14, pp. 207-221, (1999).
Felberbaum et al., "Ovarian Stimulation for assisted reproduction with Hmg and concomitant midcycle administration of the GnRH antagonist cetrorelix according to the multiple dose protocol: a prospective uncontrolled phase Iii study," Hum. Reprod., (Abstract), vol. 15, No. 5, p. 1015-20, (May 15, 2000).
Haviv et al., "In vitro and in vivo activities of reduced-size antagonists of luteinizing hormone-releasing hormone," J. Med. Chem., (Abstract), vol. 37, No. 5, pp. 701-705, (Mar. 4, 1994).

(Continued)

*Primary Examiner* — Christina Borgeest
(74) *Attorney, Agent, or Firm* — Pillsbury Winthrop Shaw Pittman, LLP

(57) ABSTRACT

A method for obtaining the production of a fertilizable oocyte within a program of assisted reproduction techniques comprising normal follicular growth and development to proceed in the absence of stimulation by an exogenous gonadotropin, followed by administering an amount of an LHRH antagonist in a dosage regimen that prevents a premature LH surge while maintaining FSH secretion at a natural level and individual estrogen development is not affected.

1 Claim, 1 Drawing Sheet

(56) References Cited

OTHER PUBLICATIONS

Huirne et al., "Cetrorelix in an oral contraceptive-pretreated stimulation cycle compared with buserelin in Ivf/Icsi patients treated with r-hFSH: a randomized, multicentre, phase IIIb study," Hum. Reprod., Epub (Abstract), vol. 21, No. 6, pp. 1408-1415, (Mar. 14, 2006).

Klingmuller et al., "Hormonal response to the new potent GnRH antagonist Cetrorelix," Acta Endocrinologica, vol. 128, pp. 15-18, (Jan. 1993).

I. Craft et al., "Will GnRH antagonists provide new hope for patients considered 'difficult responders' to GnRH agonist protocols?" Human Reproduction, vol. 14, No. 12, p. 25959-2962, (1999).

Jennings et al., "In Vitro fertilisation. A Review of Drug Therapy and Clinical Management," Drugs, vol. 52, No. 3, pp. 313-343, (Sep. 1996).

Leroy et al., "A Single Injection of a Gonadotropin-Releasing Hormone (GnRH) Antagonist (Cetrorelix)* Postpones the Luteinizing Hormone (LH) Surge: Further Evidence for the Role of GnRH During the Lh Surge," Fertility and Sterility, vol. 62, No. 3, pp. 461-467, (Sep. 1994).

Nelson et al., "Suppression of follicular phase pituitary-gonadal function by a potent new gonadotropin-releasing hormone antagonist with reduced histamine-releasing properties (ganirelix)," Fertil. Steril., (Abstract), vol. 63, No. 5, pp. 963-969, (May 1995).

Nestor, Jr. et al., "Potent gonadotropin releasing hormone antagonists with low histamine-releasing activity," J. Med. Chem., Institute of Bio-Organic Chemistry, vol. 35 No. 21, pp. 3942-3948, (Oct. 16, 1992).

Olivennes et al., "Scheduled Administration of a Gonadotrophin-Releasing Hormone Antagonist (Cetrorelix) on Day 8 of In-Vitro Fertilization Cycles: a Pilot Study," Human Reproduction, vol. 10, No. 6, pp. 1382-1386, (Jun. 1995).

Olivennes et al., "The Single or Dual Administration of the Gonadotropin-Releasing Hormone Antagonist Cetrorelix* in an in Vitro Fertilization-Embryo Transfer Program," Fertility and Sterility, vol. 62, No. 3, pp. 468-476, (Sep. 1994).

Reissmann et al., "Development and Applications of Luteinizing Hormone-Releasing.Hormone Antagonists in the Treatment of Infertility: an Overview," Human Reproduction,.vol. 10, No. 8, pp. 1974-1981, (1995).

Rivier et al., "Gonadotropin releasing hormone antagonists:novel structures.incorporating n. omega-cyano modified guanidine moieties," Biochem. Biophys. Res.Commun., (Abstract), vol. 176, No. 1, pp. 406-412, (Apr. 15, 1991).

Rivier et al., "Gonadotropin-releasing hormone antagonists with n. omega-.triazolylornithine, -lysine, or-p-am inophenylalanine residues at positions 5 and 6," J. Med.Chem., Salk Institute for Biological Studies (La Jolla, California ), vol. 35, No. 23, pp.4270-4278, (Nov. 13, 1992).

Stoeckemann et al., "Effects of the luteinizing-hormone-releasing hormone (Lhrh).antagonist ramorelix (hoe013) and the Lhrh agonist buserelin or.dim ethylbenz[]anthrracene-induced mammary carcinoma: studies with slow-release.formulations," J. Cancer Res. Clin. Oncol., Hoechst Ag, Pharma-Research.(Frankfurt/Main, Germany), vol. 119, No. 8, pp. 457-462, (1993).

Weinbauer et al., "Comparison of the antigonadotropic activity of three GnRH.antagonists (Nal-Glu,Antide and Cetrorelix) in a non-human primate model (Macaca.fascicularis)," Andrologia, Institute of Reproductive Medicine of the University (Munster,.Germany), vol. 25, No. 3, pp. 141-147, (May-Jun. 1993).

Engel et al., "Use of cetrolix in combination with clomiphene citrate and gonadotrophins: a suitable approach to 'friendly Ivf'?", Engel et al., Human Reproduction, vol. 17, No. 8, pp. 2022-2026, 2002.

Griesinger et al., "Gonadotropin-Releasing Hormone Antagonists for Assited Reproductive Techniques" Drugs 2004; 64 (6): 563-575.

Hwang et al., "Ovarian stimulation by clomiphene citrate and hMG in combination with cetrorelix acetate for Icsi cycles", Human Repoduction, vol. 18, No. 1, pp. 45-49, 2003.

Nikolettos et al., "Gonadotropin-releasing hormone anatagonist protocol: a novel method of ovarian stimulation in poor responders", European Journal of Obstetrics & Gynecology and Reporductive Biology, 97 (2001) 202-207.

Tavaniotou et al., "The impact of Lh Serum concentration on the clinical outcome of Ivf cycles in patients receiving two regimens of clomiphene citrate/gonadotrophin/0.25 mg cetrorelix", Reproductive BioMedicine Online. 2003. 6: 421-426.

* cited by examiner

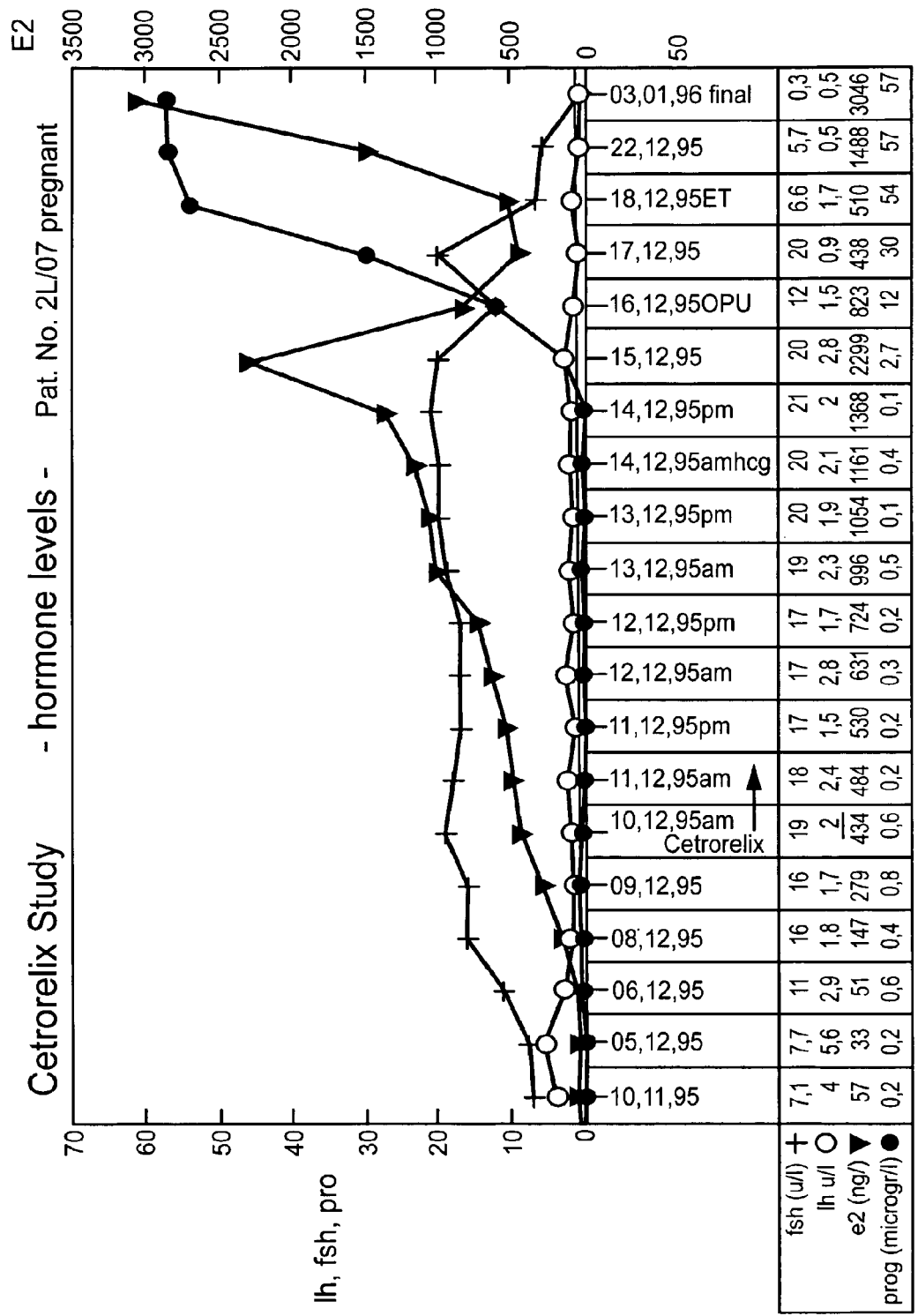

LHRH—ANTAGONISTS IN THE TREATMENT OF FERTILITY DISORDERS

CROSS REFERENCE TO RELATED APPLICATIONS

This is a continuation of U.S. patent application Ser. No. 08/786,937, filed Jan. 22, 1997, now abandoned.

This application is based on provisional application Ser. No. 60/011,282 filed Feb. 7, 1996, the content of which is incorporated herein by reference.

FIELD OF THE INVENTION

The field of invention is directed to the use of LHRH-antagonists to treat male and female fertility disorders.

BACKGROUND OF THE INVENTION

The reasons for unsuccessful attempts to establish pregnancy can be attributed equally to male and female fertility disorders. Today many different assisted reproduction techniques are available. These techniques are used to induce multiple and synchronous follicular growth and thereby obtain fertilizable oocytes.

The current standard treatment is to induce multiple follicular development by administering high doses of HMG (Human Menopausal Gonadotropin). This results in ovarian hyperstimulation. Upon reaching a suitable degree of oocyte maturation using these techniques, ovulation is induced by the administration of HCG (Human Chorion-Gonadotropin) in order to obtain a sufficient number of oocytes. During this time, the clinic-infrastructure preparation can begin. Preparation includes recovery of oocytes by abdominal or transvaginal puncture, intracorporal or extracorporal fertilization of oocytes by different techniques and embryo replacement into the uterus. Routinely, beginning pregnancy is supported by additional administrations of HCG or progesterone. Today this treatment is applied to clinical conditions of male and female infertility.

Complications that are frequently observed during the hyperstimulation procedure are:

A: premature surges of luteinizing hormone (LH) at a premature maturation state with a rupture of the follicles that induced a subsequent cancellation of the treatment occurring in about 25% of the patients; and B: ovarian hyperstimulation syndromes induced by exogenous gonadotropins which in severe cases require hospitalization and are life-threatening.

In order to avoid premature LH-surges, today LHRH-agonists are used as a comedication. By continued administration of these drugs, a complete suppression of endogenous gonadotropins is achieved by desensitization of pituitary cells and down-regulation of their receptors. Subsequently, the gonadotropin levels can be controlled by exogenous injection and the pituitary is refractory to the stimulation of LH-release by increasing levels of estradiol. Disadvantages are 1) a long treatment period until the suppression and down-regulation occur; 2) estrogen withdrawal symptoms; 3) disturbance of the normal menstrual cycle; 4) the need for frequent hormone determinations in order to evaluate the time of onset of suppression; and 5) high dose HMG treatment is needed for ovarian stimulation.

The pathogenesis of hyperstimulation syndrome is not completely understood, but is thought to be associated with the use of HCG for ovulation induction and luteal phase support.

One recent approach involves the use of the LHRH antagonist Cetrorelix (INN). In first clinical trials, short term treatment with Cetrorelix resulted in a complete avoidance of premature LH surges during stimulated cycles and the need for HMG. Due to the immediate suppression of gonadotropins by this antagonist, the unwanted stimulatory phase and also the withdrawal of estrogen produced by the agonists was avoided. The duration of treatment was also significantly shortened. In addition, it was shown that a single injection of an antagonist, given in the mid-follicular phase, would adequately suppress premature LH surges.

SUMMARY OF THE INVENTION

Despite the improvements described above, these treatment modalities suffered the drawback of treating the patients with the highest possible dose of exogenous gonadotropins to hyperstimulate multiple follicular development which results in some severe adverse events.

The current invention reduces the severe adverse events, improves patient compliance and reduces costs. Recent data obtained with Cetrorelix also demonstrates additional surprising new advantages for the treatment of male and female infertility.

In animal experiments and clinical studies with Cetrorelix, it was possible to induce an arrest of the normal, unstimulated follicular growth by multiple or single injections. These effects were observed with extremely low dosage levels. These low dosage levels present new possibilities for manipulating the time of ovulation during a normal, not exogenous gonadotropin-stimulated cycle, without affecting the viability of the growing follicle. In case of inadequate follicular growth related to treatment with LHRH-antagonists, low dose and short term administration of gonadotrophin or other trophic compounds will compensate for these effects. Subsequently, by stopping the LHRH-antagonist treatment, it is possible to let the normal ovulation occur or to induce ovulation by exogenous manipulation, if necessary. Ovulation induction was induced by the administration of standard HCG or by administration of LHRH and/or LHRH agonistic analogs.

These described treatment alternatives are a departure from existing protocols, since they are possible only if preceded by treatment for LH-surge-control with an LHRH-antagonist. In animal and clinical studies with Cetrorelix it was shown that the responsiveness of the pituitary to LHRH or agonistic analogs is preserved under these conditions of treatment. Without this treatment, the pituitary cannot respond after agonistic pretreatment for LH-surge control due to receptor down-regulation. In addition, the possible use of ovulation inducing agents other than HCG results in a reduced incidence of ovarian hyperstimulation syndrome.

On the basis of the described results, for the first time it is possible to use normal, non-gonadotropin-stimulated cycles for assisted reproduction techniques, including sperm injections, by determining the time of ovulation by the duration and dose of Cetrorelix given. Especially in conjunction with the method of ICSI (Intra-Cytoplasmatic-Sperm-Injection) this antagonist-dependent treatment modality facilitates the inclusion of in-(sub-)fertile males into this kind of fertility treatment. Due to the direct injection of male gametes capable for fertilization, this method has a high success rate and hence, allows the harvest of only one follicle for fertilization. In addition, the use of LHRH-antagonists like Cetrorelix in the described manner relieves the patient from severe ovarian hyperstimulation and significantly reduces the costs of a treatment cycle.

LHRH-antagonists of the invention can be used in combination with assisted reproduction techniques, especially the extracorporal fertilization, e.g. the in-vitro fertilization and the sperm injection techniques.

Compounds with the desired LHRH-antagonistic activity include a LHRH-analog such as Ganirelix, Antarelix, Antide, Azaline B, Ramorelix, A-76154, Nal-Glu, 88-88, in particular Cetrorelix or a structure-truncated peptide with LHRH-antagonistic activity or a peptideomimetic with LHRH-antagonistic activity, for example D-23980 and D-24824, or a bicyclic (1-4. 4-10) LHRH analog with antagonistic activity.

LHRH-antagonists of the invention can be subcutaneously administered in dosage amounts of about 0.001-0.2 mg/kg.

Both dosing schedules demonstrate the prevention of any premature LH surge. After both posologies good fertilization rates have been obtained with good follicle and oocytes quality. Pregnancy rates are good after both treatments. To date, a total of 44 healthy babies are born following both treatments.

The single dose regimen requires only one single injection of 3 ml. This has to be regarded as being convenient for the patient. So far, duration of effect to prevent a premature LH surge is up to 6.5 days. After 3 days, monitoring of hormones is advisable in order to apply a second injection in case of a low responder to HMG with prolonged administration of HMG, and if an increase of LH values is seen.

The multiple dose schedule requires daily injections of 1 ml for 3 to 7 days, sometimes up to 10 or 14 days. This is not as convenient as a single or dual injection. On the other hand, regular monitoring of the hormones is not required and the application of HCG could even be extended if required in rare cases.

In summary, from a medical point of view, both treatments show comparable efficacy, safety and practicability, therefore each should have the possibility to decide upon the dosing schedule with respect to the situation observed in each single patient.

The results of a phase II clinical trial are shown in Table I. A total of 235 patients were treated.

No premature LH surge was seen in any patient undergoing COS/ART treated with either multiple doses of 0.25 mg or higher or a single dose of 3 mg or higher. During multiple dosing, the mean days of Cetrorelix application is 6 days. 25 babies were born by the end of May 1996 (7 following multiple doses; 18 following single/dual doses).

BRIEF DESCRIPTION OF THE DRAWING

FIG. 1 depicts the time variation of various hormonal levels.

TABLE I

Cetrorelix Development Controlled Ovarian Stimulation (COS/ART)

| Subj. Nos. | Phase | Dose/Day (mg) | Posology (days) |
|---|---|---|---|
| 14 | II/proof concept | 3 | 3-10 |
| 19 | II/proof concept | 1 | 3-10 |
| 11 | II/proof concept | 0.5 | 3-10 |
| 32 | II/ | 0.5 | 3-7/14 |
| 30 | dose finding/ | 0.25 min. effect. dose | |
| (28) | minimal effective dose | 0.10 no effect. dose | |
| 21 | II/proof concept | 5 | 1 or 2 |
| 18 | II/proof concept | 3 | 1 or 2 |
| 32 | II/dose finding/ | 3 min. effective dose | 1 |
| 30 | minimal effective dose | 2 no effect. Dose | 1 |
| SUM Phase II | 235 finished | 71 pregnancies (30%) 16 pregnancies (ongoing) | 44 healthy children |

The main advantages in controlled ovarian stimulation (COS/ART) with Cetrorelix are:

1. New therapeutic principle
   a) Prevention of premature LH-surges
   b) Uniform and continuous follicular synchronization
   c) Uniform and continuous estradiol development
   d) Very low LH-values for optimal follicular development
2. Short term treatment of 3 to 7 days to max 14 days
   a) Short-term exposure during follicular development
   b) Low medication exposure during follicular development
3. No flare-up but immediate hormonal response
4. No pretreatment for 14 to 21 days before start of HMG needed
5. Fits well into normal menstrual cycle with
   a) No modification of physiological menstrual cycle pattern or
   b) No hormonal withdrawal syndromes before stimulation
6. No or only ultrashort-term residual effects after ovulation induction
7. No residual effects during and following embryo transfer
8. No ovarian cyst formation before start of stimulation
9. Reduction of HMG.

Table II (flow chart) shows an example on a typical treatment start and duration of HMG and Cetrorelix in patients to undergo controlled ovarian superovulation for ART.

TABLE II

Summary of assessments
(Flow-chart)

| PERIOD: | hMG[2] PERIOD d1 → until day of hCG: | | | | hCG[4] apply if: lead follicle: ≥20 mm φ or $E_2$ ≥ 1,200 pg/ml | Post hMG PERIOD | | | |
|---|---|---|---|---|---|---|---|---|---|
| Treatment/ Investigations | | | Cetrorelix | | | | | | |
| Parameters: | pre | hMG day 1[1] Cycle day 2 or 3 | hMG days d2-d5 | hMG day d6 | hMG day[2] d7 until the day of hCG | cancel, if: ≥12 foll. ≥15 mm φ or $E_2$ ≥ 4,000 pg/ml (≥14,684 pmol/l) | OPU | ET | 6-8 days after ET | Final Docum.: Day 20-25 after ET |
| Screening data | X | | | | | | | | | |
| End of Trial Form | | | | | | | | | X[5] | Pregnancy and Baby follow up Follow up: replacement cycles |
| Cetroreloix 0.25 mg s.c. daliy | | | X | X | X | | | | | |
| hMG inj. (2/3/4+) → hCG 10,000 IU l.m. injection | | X[1] 2 Amp | X 2 Amp | X 2+++ Amp | X[2] 2+++ Amp | X[2] 2+++ Amp X[3] | | | | |
| Ultrasound (USS) | X | X | | (X) optional | (X) optional | X | X | | X | |
| Hormones: (hCG) LH, FSH, $E_2$, P | X | X[1] | | X | X daily | X[7] 2-times: morning + just before hCG | X | X | X | X |
| Lab(Hemat., clin. chem.) | X | | | X | | | X | | X | |
| Luteal phase support → hCG or Progesterone. | | | | | | | | X[5] | X[6] | |
| Tolerability/AE's | X | | | | at every visit | | | | | |

X[1] = 1st day (d 1) of hMG injection: after comfirmation (verified in the morning) of: menstrual bleeding; no pregnancy: hCG → neg. (≤10 IU/l); P ≤ 1 ng/ml (≤3.81 nmol/l); FSH ≤ 10 IU/l; no ovarian cyst (≥2 cm φ producing $E_2$ ≥ 50 pg/ml (≥185 pmol/l)). d1 of hMG = day 2 or 3 of menstrual cycle I
X[2] = last day of hMG administration depends on follicle maturation (see X[3]).
X[3] = day of injection of 10.000 IU hCG; as soon as at least 1 follicle with a mean diameter of 20 mm, measured by ultrasound (USS) or $E_2$ ≥ 1 200 pg/ml (≥4 405 pmol/l), is observed.
X[4] = CAVE: In case of >12 follicles ≥ 15 mm φ or $E_2$ ≥ 4 000 pg/ml (≥14 684 pmol/l) during stilmulation period → no hCG injection I → Cycle cancellation I
X[5] = Luteal phase support to centre's rule: Either injections of hCG according to centre's rule or vagin. application of Progesterone (e.g. 3 × 200 mg/day) will be given accord. to centre's rule.I
X[6] = Must always be documented in any case of any premature study termination (e.g. in case of any Drop out).
X[7] = Blood samples for hormone determination on the day of hCG will be withdrawn 2 times (morning and just before hCG application) at hospital or oulsite.
Ultrasound (USS): (X) will be undertaken according to centre's rule between day 6 of hMG until the day of hCG I USS has to be performed on the day of HCG!

EXAMPLE 238 patients were treated with Cetrorelix by subcutaneous injection of Cetrorelix Acetat-Lyophilisat.

134 patients were treated with multiple doses and 104 patients with single or dual doses. The multiple doses are 0.25 mg/day or higher. The single dose was 3 mg or higher. No premature LH surge was seen in any patient undergoing controlled ovarian superovulation for assisted reproduction technology (COS/ART) treated with these dosages. Multiple doses were applied for 3 to a maximum of 10 days dependent on follicular development.

As a result 71 pregnancies were obtained=30.0%
38 of 134 following the multiple does regimen=28.4%
33 of 104 following the single/dual dosage regimen=31.7%

Following treatment 44 babies were born that means 15 following multiple does and 29 following single/dual does. 16 pregnancies are still ongoing. FIG. 1 shows this in particular.

FIG. 1 shows an absolute prevention of any premature LH surge. Furthermore, FSH secretion is maintained at a natural level and therefore the individual estrogen development is not affected.

What is claimed is:

1. A method for obtaining the production of a fertilizable oocyte within a program of assisted reproduction techniques in a female human selected for controlled ovarian stimulation, consisting of:
   (a) allowing normal follicular growth and development to proceed in the absence of stimulation by an exogenous gonadotropin;
   (b) administering an amount of LHRH antagonist Cetrorelix in a dosage regimen that prevents a premature LH surge, beginning on menstruation cycle day 1 to 10;
   wherein follicular growth and development proceeds in the absence of a LH surge and a fertilizable oocyte is produced, ovulation occurs between day 9 and 20 of the menstruation cycle,
   wherein said amount of Cetrorelix is administered by a dosage regimen of from 0.25 to 0.5 mg/day for 3 to 10 days,
   wherein said amount of said Cetrorelix does not suppress endogenous FSH secretion, which is maintained at a natural level and individual estrogen development is not affected.

* * * * *